US00PP13101P2

(12) United States Plant Patent
Pieters

(10) Patent No.: US PP13,101 P2
(45) Date of Patent: Oct. 22, 2002

(54) CHRYSANTHEMUM PLANT NAMED 'YELLOW URANO'

(76) Inventor: Dirk Pieters, Schierveldestraat 3A, Oosnieuwkerke, 8840 Staden (BE)

( * ) Notice: Subject to any disclaimer, the term of this patent is extended or adjusted under 35 U.S.C. 154(b) by 0 days.

(21) Appl. No.: 09/550,153

(22) Filed: Apr. 17, 2000

(51) Int. Cl.[7] ..... A01H 5/00
(52) U.S. Cl. ..... Plt./295
(58) Field of Search ..... Plt./295

(56) References Cited

U.S. PATENT DOCUMENTS

PP6,771 P * 5/1989 VandenBerg ..... Plt./295

OTHER PUBLICATIONS

UPOV–ROM GTITM Computer Database, 2001/06, GTI Retrieval Software, citation for 'Yellow Urano'.*

* cited by examiner

*Primary Examiner*—Bruce R. Campell
*Assistant Examiner*—Susan B. McCormick
(74) *Attorney, Agent, or Firm*—Christie, Parker & Hale, LLP

(57) ABSTRACT

A new plant variety of chrysanthemum producing yellow flowers.

1 Drawing Sheet

BACKGROUND OF THE INVENTION

The present invention is directed to a new and distinct variety of *Chrysanthemum morifolium*. The varietal denomination of the new chrysanthemum is 'YELLOW URANO'.

The new variety is a natural mutation discovered in a controlled planting of the variety 'Red Urano' (pending U.S. Plant patent; application Ser. No. 09/550,156) in Staden, Belgium. The new variety has been asexually reproduced by vegetative cuttings in Ventura County, Calif. and the distinguishing characteristics are retained through successive generations of asexual reproduction.

SUMMARY OF THE INVENTION

'YELLOW URANO' is a floriferous chrysanthemum plant that produces yellow flowers.

COMPARISON WITH PARENTS

'YELLOW URANO' differs from its parent in having yellow ray florets whereas its parent has red ray florets.

BRIEF DESCRIPTION OF ILLUSTRATIONS

The accompanying photograph shows a typical specimen of the plant and flowers of the new variety with colors being as nearly true as possible with illustrations of this type.

DESCRIPTION OF THE PLANT

The following description of the new variety is of specimens grown in a greenhouse in Ventura County, Calif. Plants described are approximately 105 days old from a rooted cutting. 'YELLOW URANO' has not been observed under all possible environmental conditions. The phenotype may vary with variations in the environment such as temperature, light intensity, day length and cultural conditions. The color designations herein are from The Royal Horticultural Society Colour Chart except where general terms are used.

To produce a commercial product the plants may be pinched once about ten days after planting. No growth retardant has been applied in the specimens described. Useful growing conditions include average night temperatures of about 17° C. to 20° C. and average day temperatures of about 20° C. to 30° C. The new variety has exhibited no susceptibility or resistance to disease. Resistance or susceptibility to insects has not been observed. Winter hardiness and drought/heat tolerance have not been observed.

ROOTING CHARACTERISTICS

Time to initiate roots: About 7 to 14 days at about 21° C.
Root description: Fine, fibrous.

PLANT

Plant type: Herbaceous perennial.
Growth habit: Mounding.
Size: Height about 23 cm, width about 25 cm.
Growth rate: Moderate.
Branching characteristics: Very free branching, lateral branches are about 20 cm in length, 0.5 cm in diameter and near 138C in color.

FOLIAGE

Arrangement: Alternate.
Compound or Simple: Simple.
Quantity of leaves: Many.
Leaf size:
*Length*.—About 5.5 cm.
*Width*.—About 3.5 cm.
Leaf shape: Shape general outline is ovate, margin is palmately lobed.
Leaf tip: Acuminate.
Leaf base: Attenuate.
Leaf attachment: Stalked.
Petiole: Length about 2 cm, diameter about 0.3 cm, color near 137C.

Margin type: Serrate.
Texture: Lightly pubescent.
Color:
*Young foliage upper side*.—Near 137A.
*Young foliage under side*.—Near 138B.
*Mature foliage upper side*.—Near 137A.
*Mature foliage under side*.—Near 137A.
Venation: Net.
*Color*.—Venation upper side: Near 137C. Venation under side: Near 137D.

BLOOM

Inflorescence:
*Flowering habit*.—Induced by darkness period greater than 13.5 hours. Approximately 50 days of day length required to induce and develop blooms.
*Inflorescence form*.—Decorative, opening to a multiplex daisy, the term multiplex daisy is used to describe many rows of ray florets and a very small disc presence. When the inflorescence ages, the disc florets become visible, creating a very small disc. For the majority of the inflorescence life, the disc is not visible and the form is decorative.
*Natural flowering season*.—Around the last week in August and early September in Ventura County, Calif.
*Quantity of inflorescences per stem*.—About 15.
*Inflorescence diameter*.—About 5 cm, the ray florets are attached at approximately a 45° angle. When removed and measured, they are individually about 4 cm. The disc is covered by ray florets, not exposed until the inflorescence ages. The description of the disc is for the diameter after the ray florets are removed and the disc is measured on its own. The diameter of the disc, because it is covered by ray florets, does not contribute to the overall diameter of the inflorescence.
*Inflorescence depth*.—About 2 cm.
*Disc diameter*.—About 1.7 cm.
*Inflorescence longevity on plant*.—About 20 to 25 days.
*Persistence*.—Persistent.
Ray florets:
*Appearance*.—Matte.
*Texture*.—Smooth.
*Number*.—About 150.
*Shape*.—Oblanceolate.
*Margin*.—Entire.
*Tip*.—Obtuse.
*Length*.—About 4 cm.
*Width*.—About 1.5 cm.
*Color*.—Upper side: First opening: Near 13A. Mature: Near 14B. Fading: Near 13B. Under side: First opening: Near 13B. Mature: Near 14B. Fading: Near 13B.
Disc florets: Pistil length is about 1 cm.
*Appearance*.—Shiny.
*Texture*.—Smooth.
*Number*.—About 70.
*Shape*.—Cylindric.
*Tip*.—Obtuse.
*Length*.—About 1 cm.
*Width*.—About 0.1 cm.
*Color*.—First opening: Near 16A. Mature: Near 13B. Fading: Near 16B.
Peduncle: About 0.3 in diameter.
*Length*.—Terminal, shortest: About 5 cm. Lateral, longest: About 9 cm.
*Color*.—Near 137A.
*Strength*.—Moderate.
*Habit*.—Erect.
Inflorescence bud:
*Length*.—About 1 cm.
*Diameter*.—About 1 cm.
*Form or shape*.—Globular.
*Color*.—Near 13A.
Involucral bracts: Length about 0.9 cm, width about 0.7 cm.
*Appearances*.—Matte.
*Texture*.—Lightly pubescent.
*Number*.—About 20 to 30.
*Shape*.—Ovate.
*Margin*.—Entire.
*Tip*.—Acute.
*Color*.—Upper side: Near 137A. Under side: Near 137A.

REPRODUCTIVE ORGANS

Ray florets:
*Pistillate*.—Pistil length in the ray florets is about 1.1 cm.
*Pistil number*.—1 per flower.
*Stigma shape*.—2 branched.
*Stigma color*.—Near 9A.
*Style length*.—About 1 cm.
*Style color*.—Near 6D.
Disc florets:
*Pistillate*.—Pistil number: 1 per flower. Stigma shape: Cylindric. Style length: About 0.8 cm.
*Staminate*.—Stamen number: About 5. Anther shape: Tubular. Anther color: Near 16A. Pollen color: Near 20A.

What is claimed is:

1. A new and distinct chrysanthemum plant of the variety substantially as herein shown and described.

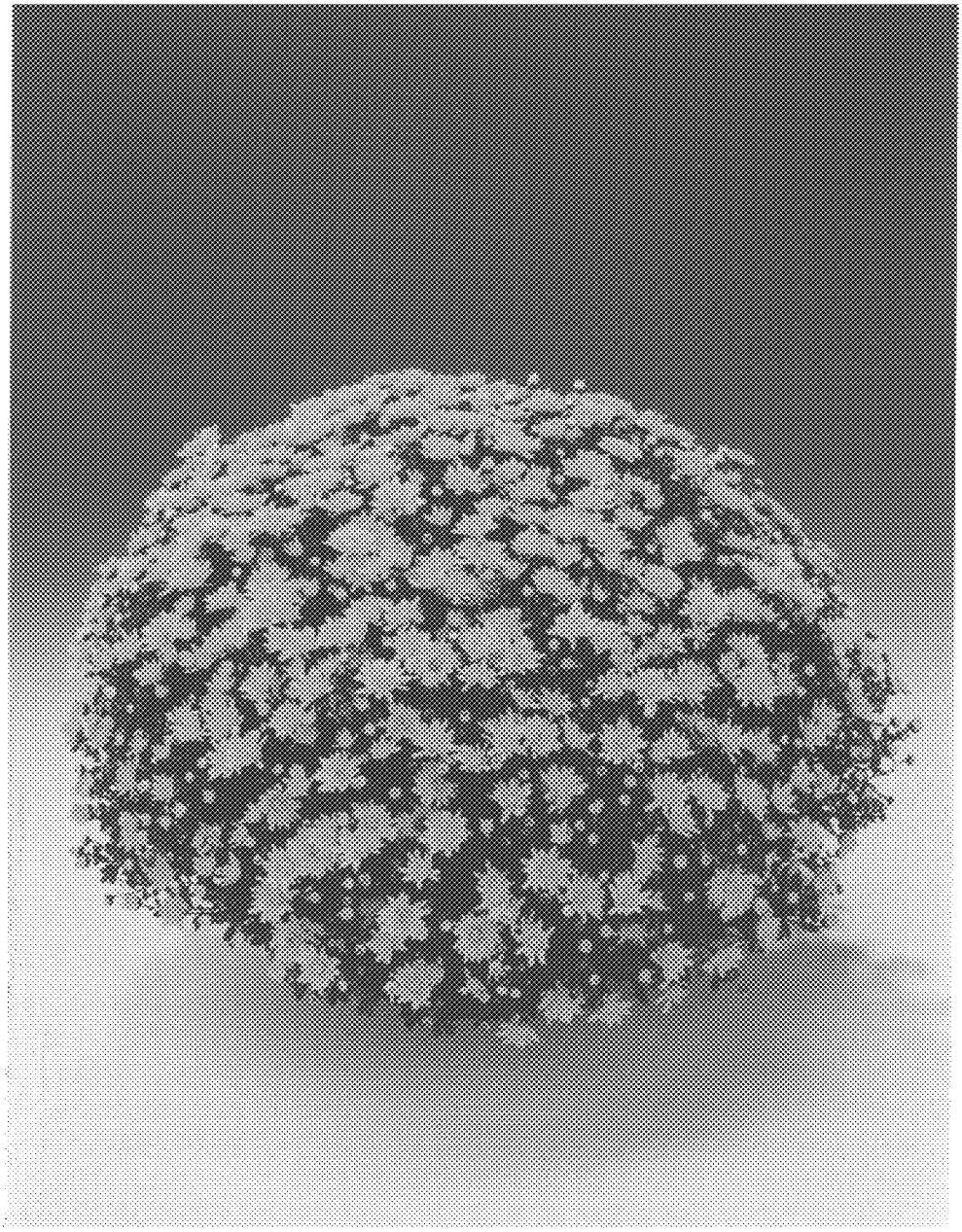

* * * * *